(12) United States Patent
Pagnoux et al.

(10) Patent No.: US 8,896,833 B2
(45) Date of Patent: Nov. 25, 2014

(54) DEVICE AND METHOD FOR DETERMINING A PIECE OF POLARIZATION INFORMATION AND POLARIMETRIC IMAGING DEVICE

(75) Inventors: Dominique Pagnoux, Limoges (FR);
Frédéric Louradour, Eymoutiers (FR);
Jérôme Desroches, Limoges (FR);
Alain Barthelemy, Limoges (FR);
Julien Brevier, Saint-Junien (FR)

(73) Assignee: Centre National de la Recherche Scientifique-CNRS, Paris Cedex (FR)

( * ) Notice: Subject to any disclaimer, the term of this patent is extended or adjusted under 35 U.S.C. 154(b) by 164 days.

(21) Appl. No.: 13/144,519

(22) PCT Filed: Jan. 15, 2010

(86) PCT No.: PCT/FR2010/050063
§ 371 (c)(1),
(2), (4) Date: Aug. 23, 2011

(87) PCT Pub. No.: WO2010/081999
PCT Pub. Date: Jul. 22, 2010

(65) Prior Publication Data
US 2011/0292389 A1 Dec. 1, 2011

(30) Foreign Application Priority Data

Jan. 15, 2009 (FR) .................................... 09 50236
May 20, 2009 (FR) .................................... 09 53402

(51) Int. Cl.
*G01J 4/00* (2006.01)
*G01J 4/04* (2006.01)
*G01N 21/21* (2006.01)
*G01N 21/84* (2006.01)
*A61B 5/00* (2006.01)

(52) U.S. Cl.
CPC ............ *G01J 4/04* (2013.01); *G01N 2021/8438* (2013.01); *A61B 5/0064* (2013.01); *A61B 5/0059* (2013.01); *A61B 5/0062* (2013.01); *G01N 21/21* (2013.01); *A61B 5/442* (2013.01)

USPC .......................................................... 356/369

(58) Field of Classification Search
CPC ......... G01J 4/04; G01N 21/211; G01N 21/21; G01N 21/23; G01N 2021/4792; A61B 5/0066; G01B 2290/70
USPC ................................................... 356/364–369
See application file for complete search history.

(56) References Cited

U.S. PATENT DOCUMENTS 4,626,679 A 12/1986 Kuwayama et al.
5,206,924 A * 4/1993 Kersey ........................... 356/478

(Continued)

FOREIGN PATENT DOCUMENTS

WO     WO 98/53272     11/1998

OTHER PUBLICATIONS

Poul M. F. Nielsen, et al Polarization-Sensitive Scanned Fiber Confocal Microscope, University of Auckland, Department of Engineering Science Date: Nov. 1, 1996 Optical Engineering 35(11), pp. 3084-3091.

(Continued)

*Primary Examiner* — Kara E Geisel
(74) *Attorney, Agent, or Firm* — Miller, Matthias & Hull LLP

(57) ABSTRACT

The invention relates to a method and to a device for determining at least one piece of polarization information on a measurement point of a target sample, the device comprising:—a light source capable of emitting a rectilinearly polarized light beam, the light beam being intended to be reflected by the measurement point;—a means for computing polarization information on the measurement point using the beam reflected by the target sample;—at least one waveguide for guiding the incident beam towards the target sample and the reflected beam towards the computing means; and—a means for rotating the polarization, capable of rotating two orthogonal polarimetric components of the incident beam after passing through the waveguide and two orthogonal polarimetric components of the reflected beam before passing through the waveguide.

15 Claims, 5 Drawing Sheets

(56) References Cited

U.S. PATENT DOCUMENTS

| | | | | |
|---|---|---|---|---|
| 5,887,009 | A | * | 3/1999 | Mandella et al. ................. 372/6 |
| 6,292,287 | B1 | | 9/2001 | Fujinoki |
| 6,385,358 | B1 | * | 5/2002 | Everett et al. ................... 385/12 |
| 7,289,211 | B1 | | 10/2007 | Walsh, Jr. et al. |
| 2005/0213103 | A1 | * | 9/2005 | Everett et al. ................. 356/479 |

OTHER PUBLICATIONS

International Search Report from corresponding International Patent Application PCT/FR2010/050063 Dated May 21, 2010.

* cited by examiner

DEVICE AND METHOD FOR DETERMINING A PIECE OF POLARIZATION INFORMATION AND POLARIMETRIC IMAGING DEVICE

CROSS-REFERENCE TO RELATED APPLICATIONS

This application is a U.S. national stage filing of International Patent Application No. PCT/FR2010/050063 filed on Jan. 15, 2010, which claims priority under the Paris Convention to French Patent Application No. 09 50236, filed on Jan. 15, 2009 and French Patent Application No. 09 53402 filed on May 20, 2009.

FIELD OF THE DISCLOSURE

The invention relates to a device and a method for determining a piece of polarisation information for a point of a target sample, as well as a polarimetric imaging device.

BACKGROUND OF THE DISCLOSURE

In particular, the invention relates to a determining device comprising:
- a light source capable of emitting a rectilinearly polarised light beam in a predefined direction, the light beam being intended to be reflected by the measurement point of the target sample,
- a means for calculating the polarisation information for the measurement point from the beam reflected by the target sample.

U.S. Pat. No. 7,289,211 describes an example of such a determining device.

Such a device for determining polarisation information provides information on the micro or nanostructure of target samples, and on their texture at the surface or slightly beneath the surface. This polarisation information can be, for example, the phase shift or the degree of polarisation of the beam returned by the target sample. This information is primarily used in the medical field for diagnosis, and in the field of microelectronics for characterizing single-layer or multilayer thin films or for analyzing complex surfaces.

Generally, the polarisation information is obtained by reflecting a polarised light beam on a target sample. Polarisation information for the target sample can be determined by analyzing the polarisation of the reflected beam.

This technique requires the use of a light beam with direct line of sight to and unencumbered space around the target area. It is not possible to measure polarisation information from an object situated in an area difficult to access, inside a cavity, or in an obscuring environment.

One goal of the invention is to overcome this disadvantage and provide a device for determining a piece of polarisation information which allows, among other things, analyzing target samples not accessible by a light beam with direct line of sight.

SUMMARY OF THE DISCLOSURE

For this purpose, one object of the invention is the determining device mentioned above, comprising:
- at least one waveguide capable of guiding the incident beam towards the target sample, and the reflected beam towards the calculation means; and
- a polarisation rotation means capable of rotating two orthogonal polarimetric components $E_\parallel^I$; $E_\perp^I$ of the incident beam after passage through the waveguide and two orthogonal polarimetric components $E_\parallel^R$; $E_\perp^R$ of the reflected beam before passage through the waveguide, to compensate for the effect of the waveguide birefringence.

In particular, the invention enables the analysis of biological tissue structures such as collagen, in vivo, in situ, with no need for biopsy.

Another object of the invention is a polarimetric imaging device for generating a polarimetric image of a target sample, said imaging device comprising:
- a device for determining a piece of polarisation information as described above, said device being capable of determining multiple pieces of polarisation information,
- a unit for constructing a polarimetric image representative of the polarisation information from measurement points of the target sample, each characteristic of a pixel of the image representing the polarisation information for a measurement point of the target sample.

A last object of the invention is a method for determining a piece of polarisation information for a measurement point of a target sample, said method comprising the following steps:
a) a step in which a rectilinearly polarised incident light beam is emitted in a predefined direction,
b) a step in which the incident beam is guided towards the measurement point of the target sample with the aid of a waveguide,
c) a step of rotating two orthogonal polarimetric components of the incident beam after passage through the waveguide,
d) a step in which the incident beam is reflected at the measurement point of the target sample,
e) a step in which two orthogonal polarimetric components of the reflected beam are rotated before passage through the waveguide,
f) a step in which the reflected beam is guided towards a calculation unit by the same waveguide,
g) a step of calculating the polarisation information for the measurement point of the target sample, based on the reflected beam recovered at the exit from the waveguide;
steps c) and e) compensating for the effect of the waveguide birefringence.

BRIEF DESCRIPTION OF THE DRAWINGS

The invention will be better understood by reading the following description, provided solely as an example, and by referring to the attached drawings in which.

In the different figures, elements denoted by the same reference refer to the same or similar elements.

DETAILED DESCRIPTION OF THE DISCLOSURE

Figure 1:
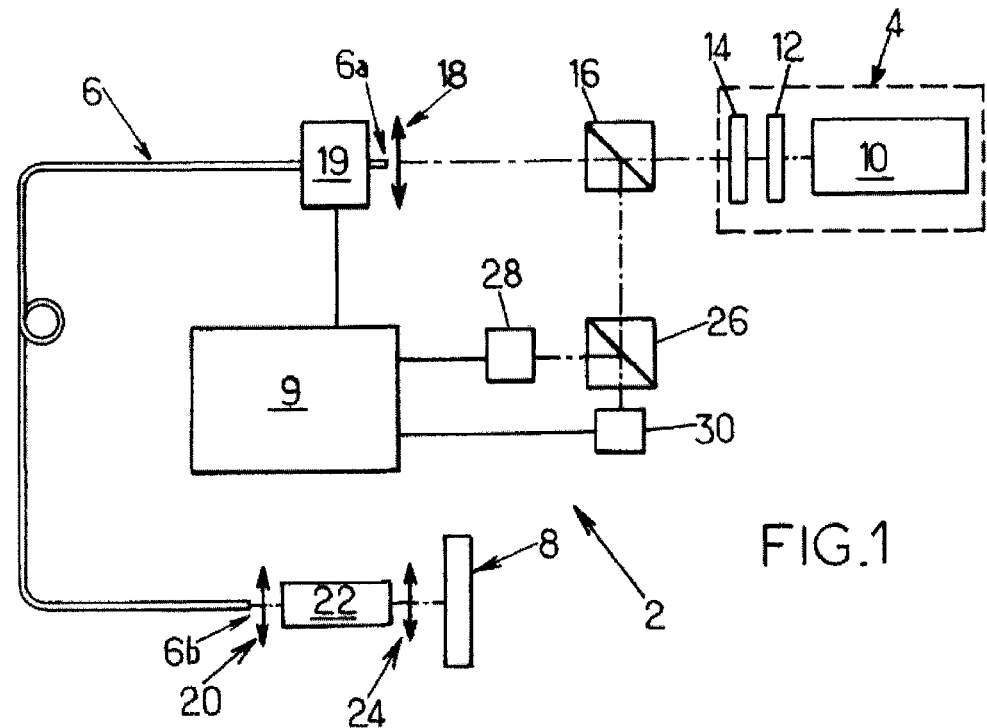
FIG. 1 is a schematic view of the determining device of the invention.

In FIG. 1, the determining device 2 comprises a monochromatic light source 4 for emitting an incident light beam, a waveguide 6 for guiding the passage of an incident beam and a beam reflected by the target sample 8, and a calculation means 9 for calculating the polarisation information based on the reflected beam recovered at the exit from the waveguide 6.

In the rest of the description, the light beam is referred to as the "incident beam" for the entire path from the source 4 to the target sample 8, and as the "reflected beam" for the entire path from the target sample 8 to the calculation means 9.

In the rest of the description, the terms "upstream" and "downstream" are defined in reference to the direction of the light beam.

The light source 4 is able to emit a rectilinearly polarised incident light beam in a predefined direction x.

This light source 4 is, for example, composed of a laser diode 10, a polariser 12, and a half-wave plate 14. The polariser 12 and the half-wave plate 14 are placed downstream from the laser diode if considering the direction of the incident beam. They are traversed by the beam emitted by the laser diode 10. The light source 4 may include a device intended to protect it from external reflections.

The determining device 2 comprises, between the light source 4 and the waveguide 6, a beam splitter cube 16 as well as a system 18 for focusing the incident beam in the waveguide 6.

The cube 16 is polarisation neutral. It only affects the intensity of the beam coming from the light source 4 and directed towards the waveguide 6. It is able to modify the direction of the reflected beam in order to direct it towards the calculation means 9.

The focus system 18 consists, for example, of a microscope objective or a convergent lens having a focal plane positioned at the entrance to the waveguide 6.

The waveguide 6 guides the incident beam onto the target sample 8, particularly when the target sample is positioned within a cavity or recess or even in the human body, where it cannot be reached by directly transmitting a light beam. It has one end 6a called the proximal end, situated near the light source 4 and calculation means 9, and another end 6b called the distal end, intended to be placed near the target sample 8.

The waveguide 6 consists of a single-mode optical fiber at the wavelength of the beam emitted by the light source 4.

A means 19 for varying the birefringence of the waveguide 6 is assembled onto the waveguide 6. This means 19 has the effect of causing the polarisation of the beam passing through the waveguide to vary. This variation means 19 consists, for example, of means able to cause the waveguide 6 to vibrate, means able to generate an electric field, or means able to cause the temperature or the pressure exerted on it to vary, in order to cause the polarisation of the beam exiting the waveguide 6 to vary over time.

The variation means 19 is connected to the calculation means 9 and is controlled by it.

Passage through the waveguide 6 modifies the incident beam so that it has two orthogonal polarimetric components $E_\parallel^I$ and $E_\perp^I$ as it exits the waveguide 6.

This modification is both due to the effect of the waveguide 6 birefringence and the effect of the polarisation variation means 19.

If considering the direction of the incident beam, the determining device 2 comprises, between the distal end 6b and the target sample 8, a first optical system 20 having the focal plane positioned at the opening in the distal end of the waveguide 6, a polarisation rotation means 22, and a second optical system 24 having the focal plane positioned at the target sample 8.

The first optical system 20 collimates the incident beam. The second optical system 24 focuses the incident beam on the measurement point of the target sample.

After reflection from the target sample 8, the reflected beam is collimated by the second optical system 24, passes through the rotation means 22, and is focused by the first optical system 20 at the entrance to the distal part 6b of the waveguide.

The rotation means 22 comprises a Faraday rotator. For medical applications, this rotator is miniaturized.

The rotator compensates for the effects of the waveguide 6 birefringence. For this purpose, it is able to rotate the two orthogonal polarimetric components $E_\parallel^I$ and $E_\perp^I$ of the incident beam exiting the waveguide 6 by an angle of 45 degrees in a given direction of rotation to obtain two polarimetric components denoted $E_\parallel^{IR}$ and $E_\perp^{IR}$. In this description, the direction of rotation is defined relative to a fixed reference point in the laboratory.

After the reflection of the incident beam from the target sample 8, the Faraday rotator rotates two orthogonal polarimetric components of the reflected beam, denoted $E_\parallel^R$ and $E_\perp^R$, by a 45 degree angle in the same direction of rotation, to obtain two orthogonal polarimetric components denoted $E_\parallel^{RR}$ and $E_\perp^{RR}$.

As the target sample 8 has modified the polarisation of the incident beam, the polarimetric components $E_\parallel^{IR}$ and $E_\perp^{IR}$ of the incident beam downstream from the rotation means 22 are different from the polarimetric components $E_\parallel^R$ and $E_\perp^R$ of the reflected beam upstream from the rotation means 24. The term downstream is defined in reference to the direction of the incident beam. The term upstream is defined in reference to the direction of the reflected beam.

The waveguide 6 guides the reflected beam towards the focus system 18.

During the second passage through the waveguide 6, the polarimetric components $E_\parallel^{RR}$ and $E_\perp^{RR}$ issuing from the rotator 22 are again modified by the waveguide 6 and by the variation means 19 in a manner identical or at least similar to the modifications occurring during the travel towards the target sample 8.

The determining device 2 additionally comprises a polarisation splitter cube 26 and two photodetectors 28, 30 connected to the calculation means 9.

The cube 26 separates a polarimetric component $E_\parallel^F$ oriented in the predefined direction x, meaning in the direction in which the light source 4 has polarised the incident beam, and a polarimetric component $E_\perp^F$ orthogonal to it.

The parallel polarimetric component $E_\parallel^F$ and the orthogonal polarimetric component $E_\perp^F$ of the reflected beam are respectively directed towards the photodetector 28 and the photodetector 30. The photodetectors 28, 30 each deliver a photocurrent, referred to hereinafter as an electric signal, to the calculation means 9.

The polarimetric components $E_\parallel^F$ and $E_\perp^F$ vary over time with the variations in polarisation generated by the variation means 19. An example of the variation in the parallel polarimetric component $E_\parallel^F$ is represented in FIG. 2 for a target sample having a 90 degree phase difference between its proper axes.

In the invention, the calculation means 9 are able to select the maximum value of the electric signal representing the parallel polarimetric component $E_\parallel^F$ as well as the corresponding value of the electric signal representing the perpendicular polarimetric component $E_\perp^F$, meaning the value measured at the same moment or in other words its minimum value.

The calculation means 9 are also able to select the minimum value of the electric signal representing the parallel polarimetric component $E_\parallel^F$ as well as the corresponding value of the electric signal representing the perpendicular polarimetric component $E_\perp^F$, meaning the value measured at the same moment or in other words its maximum value.

Figure 2:
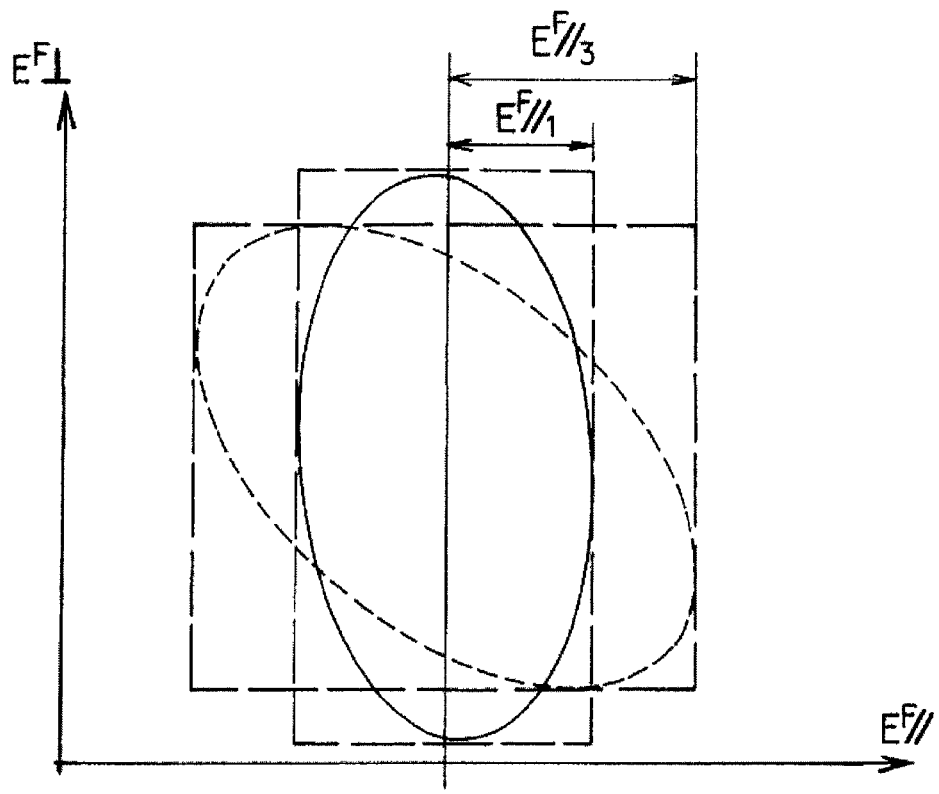
FIG. 2 is a graph representing the evolution over time of the perpendicular polarimetric component of the electric field as a function of the parallel polarimetric component.

In the example illustrated in FIG. 2, the maximum parallel polarimetric component is the polarimetric component $E_{\|3}^F$.

The calculation means 9 calculate the degree of polarisation (DOP) of the beam coming from the measurement point of the target sample based on the following formula:

$$DOP = 1 - 2K \text{ where } K = P_{\|min}/(P_{\perp max} + P_{\|min})$$

in which:

$P_{\|min}$ is the minimum power obtained based on the minimum value of the electric signal selected by the calculation means 9. It is representative of the parallel polarimetric component $E_{\|}^F$ of the electric field. $P_{\perp max}$ is the power representative of the perpendicular polarimetric component $E_\perp^F$ of the electric field measured at the same moment.

$(P_{\perp max} + P_{\|min})$ is the total power collected by the photodetectors 28 and 30. This power does not vary from one measurement to another.

Thus, if $P_{\|min}=0$ then DOP=1 which indicates that the target sample is non-depolarising; if $P_{\|min}=P_{\perp max}$ then DOP=0, which indicates that the target sample is completely depolarising.

The calculation means 9 are also able to calculate the phase shift $\theta$ introduced between the proper axes of the target sample based on the following formula:

$$\sin^2\left(\frac{\theta}{2}\right) = \frac{(1-K) \cdot P_{\|max} - K \cdot P_{\perp min}}{(1-2K)(P_{\|max} + P_{\perp min})}$$

in which:

$P_{\|max}$ is the maximum power obtained based on the maximum value of the electric signal selected by the calculation means 9. It is representative of the parallel polarimetric component $E_{\|}^F$ of the electric field.

$P_{\perp min}$ is the power representative of the perpendicular polarimetric component $E_\perp^F$ of the electric field measured at the same moment.

In a variation, the calculation means 9 is able to select the mean value of the electric signal representative of the parallel polarimetric component $E_{\|}^F$ as well as the corresponding value of the electric signal representative of the perpendicular polarimetric component $E_\perp^F$ measured at the same moment. In this case, the calculation means 9 is able to calculate the associated phase shift at the measurement point of the target sample when it is not depolarising, based on the following formula:

$$\theta = f(x) \text{ where } x = P_{\|mean}/(P_{\perp mean} + P_{\|mean})$$

in which:

f is a continuously increasing function between 0 and 180° when x varies from 0 to 1.

$P_{\|mean}$ is the mean power obtained based on the mean of several measurements of the electric signal representative of the parallel polarimetric component $E_{\|}^F$ associated with a given point of the target.

$(P_{\perp mean} + P_{\|mean})$ is the mean power collected by the photodetectors 28 and 30 during a predefined period of time.

In a variation, the waveguide 6 is a multi-mode optical fiber.

Figure 3:
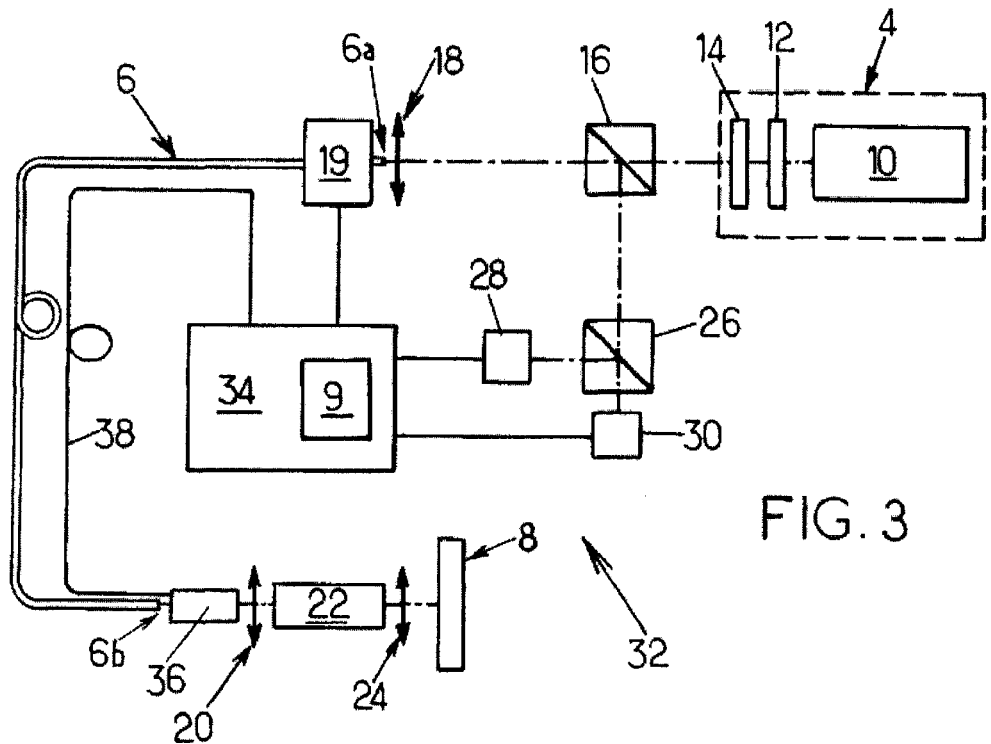
FIGS. 3 to 6 are schematic views of a polarimetric imaging device in four embodiments of the invention.

FIG. 3 represents a polarimetric imaging device 32 in a first embodiment of the invention. The imaging device 32 is formed of a device 2 for determining a piece of polarisation information, as described above, equipped with a polarimetric image construction unit 34 and a scanning system 36.

The construction unit 34 receives the values for the degree of polarisation of the beam and the phase shift values from several measurement points in the target sample 8, and constructs two polarimetric images from these. Each grayscale or each chrominance of a pixel in the first image represents the degree of polarisation associated with a measurement point of the target sample. Each grayscale or each chrominance of a pixel in the second image represents the phase shift at a measurement point of the target sample.

The image construction unit 34 is synchronized with the scanning system 36 for this purpose.

The scanning system 36 is able to direct the incident beam towards several measurement points of the target sample 8.

It is placed downstream from the waveguide 6 if considering the direction in which the incident beam travels. In particular, it is placed between the distal end 6b of the waveguide and the first optical system 20.

It consists, for example, of two mirrors which oscillate, one on a vertical axis, the other on a horizontal axis, at a frequency corresponding to the frequency at which images are constructed by the construction unit 34. It is connected to the construction unit 34 by an electric wire 38.

Figure 4:
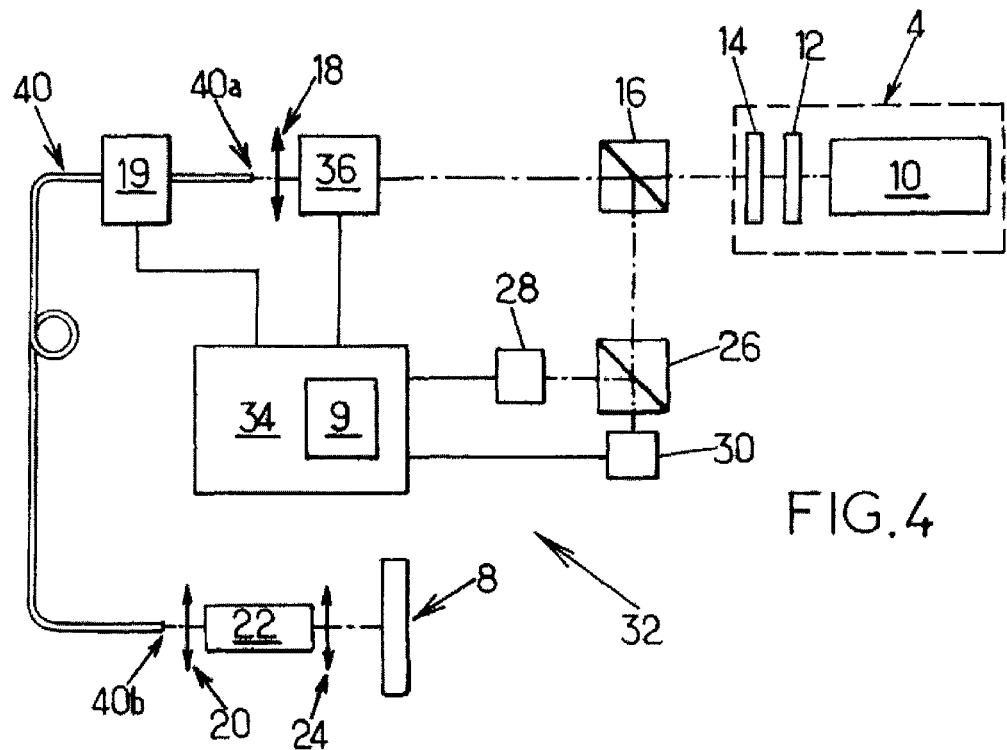

FIG. 4 represents a polarimetric imaging device 32 in a second embodiment of the invention. It is similar to the imaging device represented in FIG. 3.

However, the waveguide 6 is replaced with several waveguides 40, or with a multi-core optical fiber, and the scanning system 36 is placed upstream from the waveguides if considering the direction of the incident beam. The scanning system 36 is able to direct the incident beam towards each waveguide in turn, such that the beam successively illuminates several measurement points of the target sample 8. The scanning system sequentially processes the reflected beam when it is received. The construction unit 34 is synchronized with the scanning system 36 so that it can assign each item of polarisation information calculated by the calculation unit 9 to a corresponding position on the target sample 8.

Figure 5:
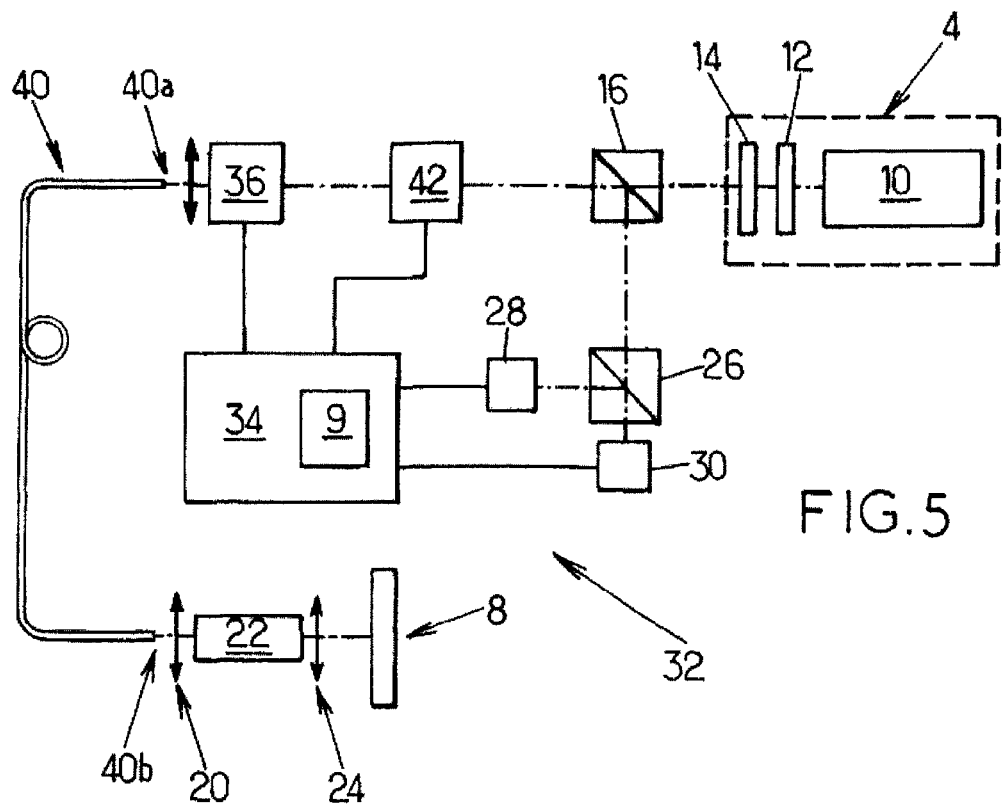

FIG. 5 represents a polarimetric imaging device 32 in a third embodiment of the invention. It is similar to the imaging device represented in FIG. 4. However, the birefringence variation means 19 are replaced with a polarisation variation means 42 placed between the cube 16 and the scanning system 36.

The polarisation variation means 42 consists, for example, of a polarisation scrambler or an arrangement of phase plates controlled by the calculation unit 9.

The polarisation variation means 42 may also be used (in place of the birefringence variation means 19) in the determining device illustrated in FIG. 1, as well as in the imaging devices illustrated in FIGS. 2 to 4.

Figure 6:
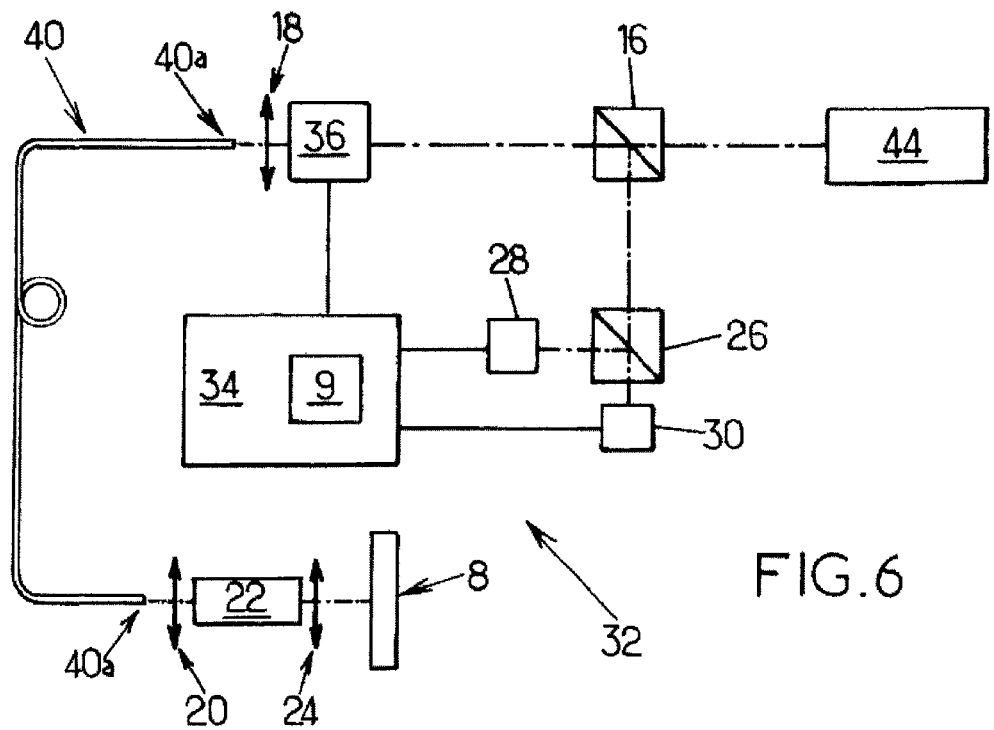

FIG. 6 represents a polarimetric imaging device 32 in a fourth embodiment of the invention. It is similar to the imaging device represented in FIG. 5. However, the monochromatic light source is replaced by a polychromatic source 44 and the polarisation variation means 42 is eliminated. The polychromatic source consists, for example, of a superluminescent diode. As the birefringence of the waveguides varies as a function of the wavelength of the beam passing through them, the variation in polarisation achieved previously by the variation means 19 or 42 is induced here by the passage of a beam of broadened spectrum through the waveguides.

In this case, the calculation means 9 is able to select the maximum value and the minimum value of the electric signal representative of the parallel polarimetric component $E_{\|}^F$ among the components of the electric field having different wavelengths. The value of the perpendicular polarimetric component $E_\perp^F$ having the same wavelength is selected for calculating the degree of polarisation and the phase shift.

Figure 7:
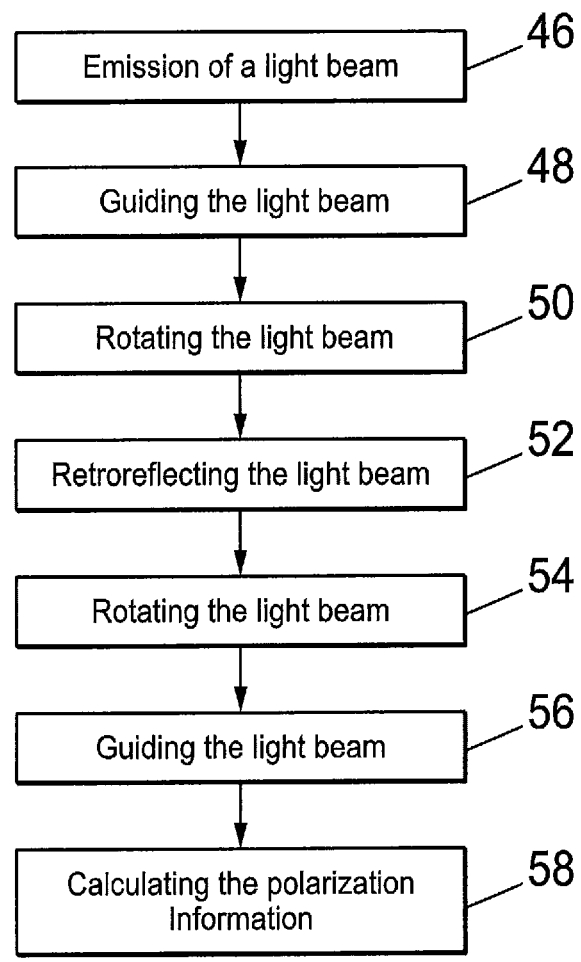
FIG. 7 is a diagram of the steps in the method of the invention.

The invention also concerns a method for determining a piece of polarisation information, illustrated in FIG. 7. The method begins with a step 46 of emitting a rectilinearly polarised incident light beam.

During a step 48, the incident beam is guided towards the measurement point of the target sample with the aid of the waveguide 6.

During a step 50, two orthogonal polarimetric components of the incident beam are rotated by a 45 degree angle by the Faraday rotator 22.

During a step 52, the incident beam is retroreflected at the measurement point of the target sample.

During a step 54, two orthogonal polarimetric components of the reflected beam are rotated by a 45 degree angle. Then the reflected beam is injected into the waveguide 6 by the optic system 20.

During a step 56, the reflected beam is guided towards the calculation unit 9 by the same waveguide 6.

Lastly, during a step 58, the polarisation information for the measurement point of the target sample is calculated based on the reflected beam recovered at the exit from the waveguide 6.

The phase shift provides, for example, information on the birefringence of the target sample while the degree of polarisation provides information on its capacity to depolarise light.

Figure 8:
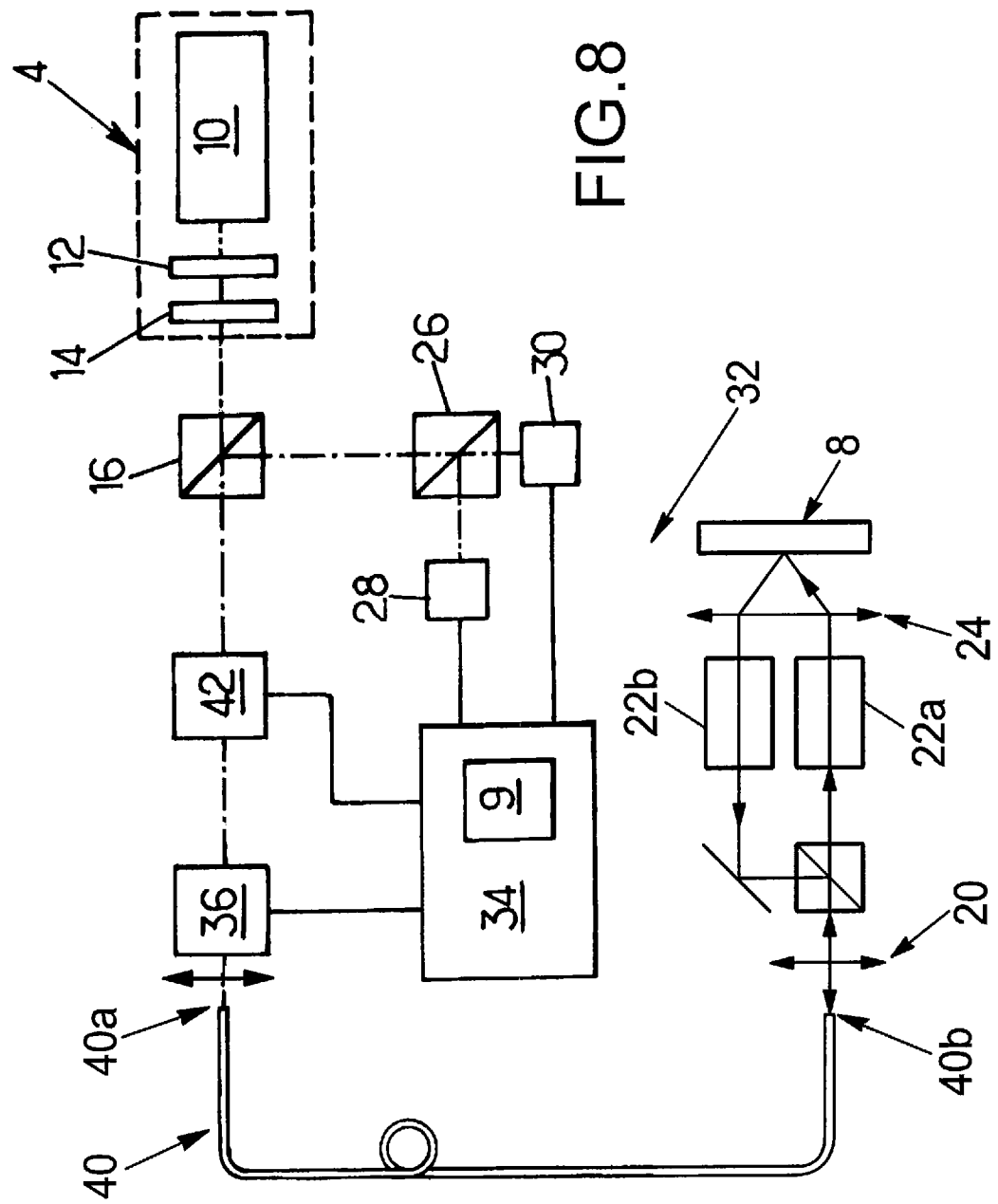
FIG. 8 is a schematic view of a polarimetric imaging device in a further embodiment of the invention.

In a variation shown in FIG. 8, the determining device 2 or the polarimetric imaging device 32 comprise a first rotator 22*a* placed only on the path of the incident beam between the distal part 40*b* and the target sample 8, and a second rotator 22*b* placed only on the path of the reflected beam between the distal part 40*b* and the target sample 8. The first rotator 22*a* is capable of rotating the polarimetric components of the beam by an angle α. The second rotator 22*b* is capable of rotating the polarimetric components by an angle 90–α degrees, where α is between 0 and 90 degrees.

In this case, the incident beam is not perpendicular to the surface of the target sample.

The invention claimed is:

1. A device for determining at least one piece of polarisation information for a measurement point of a target sample, said device comprising:
    a light source configured to emit a rectilinearly polarised incident light beam in a predefined direction, the incident light beam being intended to be reflected by the measurement point of the target sample as a reflected light beam,
    a calculation unit,
    at least one waveguide configured to guide the incident light beam towards the target sample and to output two orthogonal polarimetric components of the incident light beam, and configured to guide the reflected light beam towards photodetectors, and
    a polarisation rotator disposed to receive the two orthogonal polarimetric components of the incident light beam output from the waveguide, and configured to rotate the two orthogonal polarimetric components of the incident light beam after passage through the waveguide and to rotate the two orthogonal polarimetric components of the reflected light beam before passage through the waveguide, to compensate for the effect of the birefringence of the waveguide, and
    photodetectors measuring the reflected light beam and delivering to the calculation unit an electric signal representative of the polarimetric component of the reflected light beam oriented in the predefined direction, called a parallel signal, and an electric signal representative of the polarimetric component perpendicular to the polarimetric component of the reflected light beam oriented in the predefined direction, called an orthogonal signal,
    wherein the calculation unit selects a value of the parallel signal, the parallel signal varying over time or as a function of the wavelength, and the calculation unit calculates the degree of polarisation (DOP), based on the following formula:

$$DOP=1-2K \text{ where } K=P_{\|s}/(P_{\perp s}+P_{\|s})$$

in which:
        DOP is the degree of polarization of the measurement point of the target sample,
        $P_{\|s}$ is the power representative of the parallel signal,
        $P_{\perp s}$ is the power representative of the orthogonal signal, and
        $(P_{\perp s}+P_{\|s})$ is the total power collected by the photodetectors.

2. A device according to claim 1, wherein the polarisation rotator is configured to rotate said polarimetric components of the incident light beam and said polarimetric components of the reflected light beam in the same direction of rotation.

3. A device according to claim 1, wherein the polarisation rotator comprises a single Faraday rotator configured to rotate said polarimetric components of the incident light beam and said polarimetric components of the reflected light beam by a 45 degree angle.

4. A device according to claim 1, wherein the polarisation rotator comprises at least two Faraday rotators configured to rotate said polarimetric components of the incident light beam and said polarimetric components of the reflected light beam, one by an angle of α degrees, the other by an angle of 90–α degrees, where α is a number between 0 and 90 degrees.

5. A device according to claim 1, wherein the waveguide comprises a proximal end intended to be placed next to the light source, and a distal end intended to be placed next to the target sample, the polarisation rotator being placed between the target sample and the distal end of the waveguide.

6. A device according to claim 1, wherein the light source is monochromatic, and in which the device further comprises means for varying the polarisation of the incident light beam and of the reflected light beam.

7. A device according to claim 1, wherein the light source is polychromatic, the chromatic dependency of the birefringence of the waveguide forming a means of varying the polarisation of the incident light beam and the reflected light beam.

8. A device according to claim 1, wherein the waveguide is a single-mode optical fiber at the or at each wavelength of the beam emitted by the light source.

9. A device according to claim 1, wherein the value of the selected parallel signal is its minimum value, or its maximum value, or its mean value.

10. A polarimetric imaging device configured to generate a polarimetric image of a target sample, with said imaging device comprising:
    a device for determining a piece of polarisation information according to claim 1, said device configured to determine multiple pieces of polarisation information,
    a unit configured to construct a polarimetric image representative of the polarisation information from measurement points of the target sample, each characteristic of a pixel of the image representing the polarisation information for a measurement point of the target sample.

11. A polarimetric imaging device according to claim 10, comprising several waveguides and a scanning system placed upstream from said waveguides when considering the direction of the incident light beam; said scanning system configured to direct the incident light beam towards several measurement points of the target sample, said scanning system being controlled by the image construction unit and being synchronized with the image construction unit.

12. A polarimetric imaging device according to claim 10, comprising a single waveguide and a scanning system placed downstream from the waveguide when considering the direction of the incident light beam; said scanning system configured to direct the incident light beam towards several measurement points of the target sample, said scanning system being controlled by the image construction unit and being synchronized with the image construction unit.

13. A method for determining at least one piece of polarisation information for a measurement point of a target sample, said method comprising the following steps:
    a) emitting a rectilinearly polarised incident light beam in a predefined direction,
    b) guiding the incident light beam towards the measurement point of the target sample with the aid of a waveguide and outputting two orthogonal polarimetric components of the incident light beam,
    c) rotating two orthogonal polarimetric components of the incident light beam after passage through the waveguide,
    d) reflecting the incident light beam at the measurement point of the target sample as a reflected light beam;
    e) rotating two orthogonal polarimetric components of the reflected light beam before passage through the waveguide, the steps c) and e) compensating for the effect of the birefringence of the waveguide;
    f) guiding the reflected light beam towards photodetectors by the same waveguide;
    g) measuring the reflected light beam and delivering to a calculation unit an electric signal representative of the polarimetric component of the reflected light beam oriented in the predefined direction, called a parallel signal, and an electric signal representative of the polarimetric component perpendicular to the polarimetric component of the reflected light beam oriented in the predefined direction, called an orthogonal signal;
    h) selecting a value of the parallel signal, the parallel signal varying over time or as a function of the wavelength; and
    i) calculating a degree of polarization (DOP), based on the following formula:

$$DOP = 1 - 2K \text{ where } K = P_{\|s}/(P_{\perp s} + P_{\|s})$$

in which:
    DOP is the degree of polarization of the measurement point of the target sample,
    $P_{\|s}$ is the power representative of the parallel signal,
    $P_{\perp s}$ is the power representative of the orthogonal signal,
    $(P_{\perp s} + P_{\|s})$ is the total power collected by the photodetectors.

14. A device for determining at least one piece of polarisation information for a measurement point of a target sample, said device comprising:
    a light source emitting a rectilinearly polarised incident light beam in a predefined direction, the incident light beam being intended to be reflected by the measurement point of the target sample as a reflected light beam,
    at least one waveguide guiding the incident light beam towards the target sample, and the reflected light beam towards photodetectors,
    a polarisation rotation means rotating two orthogonal polarimetric components of the incident light beam after passage through the waveguide and two orthogonal polarimetric components of the reflected light beam before passage through the waveguide, to compensate for the effect of the birefringence of the waveguide,
    photodetectors measuring the reflected light beam and delivering to a calculation unit an electric signal representative of the polarimetric component of the reflected light beam oriented in the predefined direction, called a parallel signal, and an electric signal representative of the polarimetric component perpendicular to the polarimetric component of the reflected light beam oriented in the predefined direction, called an orthogonal signal;
    the calculation unit selecting a value of the parallel signal, the parallel signal varying over time or as a function of the wavelength, the calculation unit calculating a phase shift θ introduced between main axes of the target sample based on the following formula:

$$\sin^2\left(\frac{\theta}{2}\right) = \frac{(1-K) \cdot P_{\|s} - K \cdot P_{\perp s}}{(1-2K)(P_{\|s} + P_{\perp s})}$$

where $K = P_{\|s}/(P_{\perp s} + P_{\|s})$
    in which:
    θ is the phase shift θ introduced between the main axes of the target sample,
    $P_{\|s}$ is the power representative of the parallel signal,
    $P_{\perp s}$ is the power representative of the orthogonal signal.

15. A device for determining at least one piece of polarisation information for a measurement point of a target sample, said device comprising:
    a light source emitting a rectilinearly polarised incident light beam in a predefined direction, the incident light beam being intended to be reflected by the measurement point of the target sample as a reflected light beam,
    at least one waveguide guiding the incident light beam towards the target sample, and the reflected light beam towards photodetectors,
    a polarisation rotation means rotating two orthogonal polarimetric components of the incident light beam after passage through the waveguide and two orthogonal polarimetric components of the reflected light beam before passage through the waveguide, to compensate for the effect of the birefringence of the waveguide,
    photodetectors measuring the reflected light beam and delivering to a calculation unit an electric signal representative of the polarimetric component of the reflected light beam oriented in the predefined direction, called a parallel signal, and an electric signal representative of the polarimetric component perpendicular to the polarimetric component of the reflected light beam oriented in the predefined direction, called an orthogonal signal,
    the calculation unit selecting a mean value of the parallel signal and a corresponding value of the orthogonal signal measured at the same moment, the calculating unit calculating a phase shift θ at the measurement point of the target sample, based on the following formula:

$$\theta = f(x) \text{ where } x = P_{\|mean}/(P_{\perp mean} + P_{\|mean})$$

in which:
    θ is the phase shift θ introduced between main axes of the target sample,
    f is a continuously increasing function between 0 and 180° when x varies from 0 to 1,
    $P_{\|mean}$ is the mean power obtained based on the mean of several measurements of the parallel signal, and
    $(P_{\perp mean} + P_{\|mean})$ is the mean power collected by the photodetectors during a predefined period of time.

* * * * *